(12) United States Patent
Otoi (10) Patent No.: US 7,489,398 B2
(45) Date of Patent: Feb. 10, 2009

(54) SPECTROPHOTOMETER

(75) Inventor: Takashi Otoi, Arida (JP)

(73) Assignee: Saika Technological Institute Foundation, Wakayama-shi (JP)

( * ) Notice: Subject to any disclaimer, the term of this patent is extended or adjusted under 35 U.S.C. 154(b) by 104 days.

(21) Appl. No.: 10/577,243

(22) PCT Filed: Oct. 27, 2004

(86) PCT No.: PCT/JP2004/015899

§ 371 (c)(1),
(2), (4) Date: Apr. 26, 2006

(87) PCT Pub. No.: WO2005/040741

PCT Pub. Date: May 6, 2005

(65) Prior Publication Data

US 2007/0081160 A1    Apr. 12, 2007

(30) Foreign Application Priority Data

Oct. 29, 2003    (JP) ............................. 2003-368176

(51) Int. Cl.
    *G01J 3/42* (2006.01)
(52) U.S. Cl. ..................................... 356/328; 356/319
(58) Field of Classification Search ................. 356/328, 356/319
    See application file for complete search history.

(56) References Cited

U.S. PATENT DOCUMENTS 4,248,536 A * 2/1981 Hijikata ..................... 356/416
5,106,190 A * 4/1992 Fukuma ..................... 356/325
5,412,468 A   5/1995 Lundberg et al.
2006/0092508 A1* 5/2006 Baun et al. ................. 359/429

FOREIGN PATENT DOCUMENTS

| EP | 0 615 115 A2 | 9/1994 |
| JP | 55-126834 | 10/1980 |
| JP | 59-19839 | 2/1984 |
| JP | 63-201538 | 8/1988 |
| JP | 64-72016 | 3/1989 |
| JP | 6-300628 | 10/1994 |
| JP | 2002-98636 | 4/2002 |

* cited by examiner

*Primary Examiner*—Kara E Geisel
(74) *Attorney, Agent, or Firm*—Kratz, Quintos & Hanson, LLP (57) ABSTRACT

A spectrophotometer, for online non-destructive optical examination of fruit or vegetables or the like avoids saturation of the data level, or the data level being too small, due to changes in rate of feeding or variation in the fruit or vegetables. Light that has passed through the fruit or other article is divided into different spectral components and received at two locations, a main light reception unit and a sample-use light reception unit. A digital value obtained from the sample-use light reception unit is compared with a predetermined reference value, Based on this comparison, the gain of a variable gain amplification circuit is set to an optimum value. The signal from the main light reception unit is passed through the variable gain amplification circuit, a zero-point correction circuit, and an A/D converter, to obtain digital data to be read for obtaining suitable wavelength characteristic data.

9 Claims, 4 Drawing Sheets

SPECTROPHOTOMETER

TECHNICAL FIELD

The present invention relates to a spectrophotometer for measuring the internal properties of articles to be measured based on the amounts of charge obtained from the group of charge accumulation type photodetection elements for receiving, of light that is emitted from light emission means, light that has been transmitted through an article to be measured and been separated into different spectral components by a spectrometer, such as a prism or diffraction grating and whereby converting the same to charge to be accumulated.

BACKGROUND ART

Firstly, a system will be described in which analysis of the internal properties of the article to be measured is conducted using for example a spectrophotometer of the front-separation type: in this system, first of all, light from the light source is divided into monochromatic light by for example a diffraction grating and is then simultaneously directed onto the article to be measured and a reference article, using for example a half-mirror. Spectral data is then obtained by receiving the respective reflected or transmitted beams by the photodetection elements, performing respective logarithmic amplification on the signals of the photodetection elements where the light is thus received, and performing differential amplification on the outputs of these, to obtain the absorbancy (OD), the analogue quantity obtained by logarithmic conversion being subjected to A/D conversion to obtain spectral data.

Secondly, a spectrophotometer of the online type which is in common practical use will be described: in this spectrophotometer, since articles to be measured such as fruit or vegetables differ considerably in their optical transmissivity in accordance with for example their type or size, ripeness, skin or density, either the exposure time or the frequency of the drive clock of for example a charge accumulation type line sensor is adjusted in accordance with the size of the articles to be measured as they are fed, or the gain of the amplification unit circuit is set beforehand such that the amount of transmitted light is not saturated even when transmitted by the largest article to be measured. For example, when for example the weigh-in line is altered in accordance with for example change in the type of article to be measured, the gain may be set at the same time as alteration of the type of article to be measured and the spectral data may be obtained by A/D conversion of the analogue quantity output with prescribed (fixed) gain, set for all cases, whilst articles to be measured which are of the same size are measured.

Considering the fact that a logarithmic amplification unit is employed in the above spectrophotometer, the following problems may arise:

(i) A zero-point correction circuit for the pixel units when the photodetection element group is driven must be inserted upstream of the logarithmic amplification unit, and this makes it difficult to cancel all of the noise of the sensor amplification circuit system, including the logarithmic amplification unit.

(ii) if we assume:
  (I) (OD)=LOG(target)–log(reference)
  (II) subtraction of offset when perfectly screened
since (I) and (II) are factors that cannot be applied simultaneously, operation cannot be performed using analogue signals. Accordingly, the target offset subtraction calculation must be performed by quantization (A/D conversion) and digital anti-logarithmic operation: this is a complicated process and of course results in reduced accuracy.

(iii) In quantization of an analogue signal using a logarithmic amplifier, the low-level region of the signal is expanded by logarithmic amplification, but compression is performed in the high level region; consequently, the amount of information in the high-level region is reduced, tending to cause a deterioration in accuracy.

(1) Regarding the method of adjusting the exposure time in accordance with the size of the articles to be measured, the amount of transmitted light changes considerably not merely with size but, in particular in the case of fruit or vegetables, even for the same type of article, with the thickness and density of the skin and ripeness (internal properties) and the like. Also, due to for example the photodetection construction of the feed line, there are restrictions such as that the exposure time has to be kept fixed: thus is not in fact possible to obtain spectral data of optimum level.

(2) There are problems when subtracting the offset data. Specifically, in order to subtract the offset from the target or reference, the anti-logarithms of the respective data must be found before the subtraction is performed. Not only is this process of finding the anti-logarithm of the target data, reference data or offset data troublesome, but, in particular in the online case, electrical offset is produced for example by the dark current of the photodetection sensor or optical leakage resulting from the construction of the feed line, which may result in a multiplication factor of several times, and this electrical offset must be accurately cancelled.

(3) There are problems concerning cancellation of noise contained in the sensor amplification circuit system. Specifically, when the time and accuracy and other factors required for anti-logarithmic operation are taken into account in the logarithmically amplified signal, it is difficult to cancel for example noise i.e. 1/f noise of the amplification system or noise produced by commercial power source frequency components. For example, it is extremely difficult to perform successive zero sampling in the analogue level with high speed and high accuracy, taking into account all the offsets (including noise) of the amplification system prior to sequentially reading the charge accumulated on the pixels of the line sensor.

When measuring the internal properties including for example sugar content and acidity of fruit or vegetables in a spectrophotometer, the internal properties cannot be directly calculated by digital operation of the various data that are quantized (digitized) by the A/D converter. In this case, first of all, the dark current wavelength data when the light is fully screened is subtracted from the data of the article to be measured and the reference data, and normalization and the like steps are performed, to obtain the ratio of the logarithms and computation such as second-order differentiation is performed on this ratio in order to cancel the offset and gradient, for example, and the difference in optical absorbance characteristic (OD ($\lambda$)) with neighboring wavelengths is thereby obtained.

From this difference, the internal properties are calculated by for example statistical processing using multiple regression and P.L.S. etc. Consequently the following problems considerably affect accuracy.

For example in the case of Wenzhou oranges, due to differences in size of the order of 40 mm to 100 mm and differences such as individual density and skin, the amount of light transmitted may typically vary by a factor of about 60: such oranges move along the conveyor in random sequence. In the case of a spectrophotometer of conventional construction, the gain of the amplifier must be set beforehand such that at the maximum point of amount of light transmitted of the spectral data of oranges whose amount of transmitted light is greatest, the output of the amplifier is not saturated and such that the level of the A/D converter is close to the maximum level. Of course, the spectral data of the oranges whose amount of transmitted light is least will have a value of the amount of transmitted light of 1/60 of the oranges whose amount of transmitted light is greatest: thus sufficient measurement accuracy cannot be obtained. As mentioned above, when the internal properties of for example fruit or vegetables are calculated from a difference by statistical processing and the like, such deterioration of measurement accuracy is typically overlooked. In particular regarding the deterioration of measurement accuracy when quantization is performed, a specific description may be given as follows.

Figure 4:
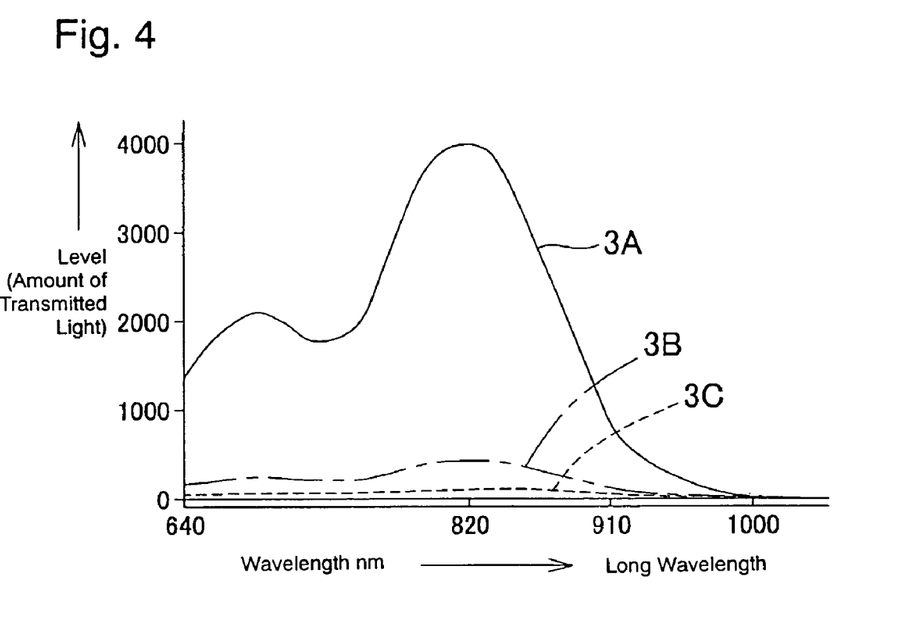
FIG. 4 Graph showing the relationship of wavelength and amount of light transmitted.

FIG. 4 shows the wavelength characteristic of oranges (articles to be measured) whose amounts of light transmitted differ by a factor of 1 to 1/60, due to differences in for example the size or thickness of the skin, when the gain is fixed. The waveform 3A indicated by the continuous line, at the top, indicates the case where the amount of light transmitted corresponds to a multiple of 1; the waveform 3B indicated by the single-dotted chain line, second from the top, indicates the case where the amount of light transmitted corresponds to a multiple of 1/10; the waveform 3C indicated by the broken line, third from the top, indicates the case where the amount of light transmitted corresponds to a multiple of 1/60. For example in the case where the articles to be measured are of the same type and have a transmitted amount of light characteristic of the same form, when two articles to be measured whose amounts of light transmitted differ for example by a factor of 10 are measured by for example the difference of size, if an A/D converter of 12 BIT (0 to 4095) resolution is employed, provisionally assuming that waves having amplitude of values 0 to ±10 reflected by sugar in the vicinity of 920 nm on the spectral data of oranges are superimposed, the A/D converted value in oranges having the largest amount of transmitted light, as indicated by the waveform 3A, is 1000, which, superimposed on the amplitude given above, results in a value of 1010 to 990.

Next, in the case of oranges having a small amount of transmitted light, as shown by the waveform 3B, the A/D converted value likewise in the vicinity of 920 nm is 1/10 thereof i.e. an A/D converter value of 101 to 99 is indicated: a wave having an amplitude of less than 10 superimposed thereon thus represents less than the minimum resolution of the A/D converter and hence is extinguished.

Of course, in the case of articles to be measured whose amounts of light transmitted differ by a factor of 1 to 60, when the optical absorbance characteristic is subjected to analysis processing such as multiple regression or P.L.S. using for example n-th order differentiation, the measurement accuracy deteriorates considerably.

Even if for example a high-resolution A/D converter is employed, there is an appreciable deterioration in the amount of information. Such deterioration of the amount of information as described above must be paid particular regard to when quantization is performed.

In the above, the case was described by way of example in which a fixed gain was set beforehand. However, a spectrophotometer has been proposed (see for example Patent Reference 1) in which there are respectively provided a first detector that detects a sample signal in the optical path on the sample side and an amplifier that amplifies the output signal from this first detector, and a second detector that detects a comparison signal in an optical path on the comparison side and an amplifier that amplifies the output signal from this second detector, comprising means for independently setting the degree of amplification (gain) of these two amplifiers.

Patent Reference 1: Laid-open Japanese Patent Application No. H. 8-101121

DISCLOSURE OF THE INVENTION

Problem that the invention is intended to solve In Patent Reference 1, detection is performed by the detectors in comparison with a sample, after spectral separation of the light from a light source by a spectrometer. Consequently, wavelength scanning must be performed by for example rotating a dispersion element such as the grating used in a spectrometer, in order to obtain the wavelength characteristic of the sample: the wavelength characteristic therefore cannot be obtained rapidly. In order to solve this problem, according to the present invention, the sample is illuminated with light from a light source and the transmitted light is spectrally separated by a spectrometer and a group of photodetection elements of a configuration in which the photodetection elements are arranged in the positions reached by the light of the respective wavelength components produced by this spectral separation is employed to obtain the wavelength characteristic of the sample without needing to perform wavelength scanning.

Also according to the present invention, a wavelength characteristic of a sample is obtained with high S/N ratio by detection utilizing the integration effect obtained by charge accumulation of weak light (minute amount of light) obtained after passing through a sample, using a small size and inexpensive charge accumulation type photodetection element group as the photodetection element group. Further according to the present invention, a further improvement in S/N ratio is obtained by performing noise reduction with an analogue circuit and performing A/D conversion with a suitable analogue level, using a zero-point compensation circuit provided immediately in front of the A/D converter.

Next, when the degree of amplification of the amplifier is determined in Patent Reference 1, a low-level threshold value and high-level threshold value are set beforehand and the gain of the amplifier is fixed such that, during photometry, the photometric value is between the low-level threshold value and the high-level threshold value. Consequently, whereas if an optimal gain is to be set for a continuously varying wavelength characteristic, the value of this gain should be a value that varies continuously with variation of the wavelength, with the method described in Patent Reference 1, only a discontinuous value can be obtained.

In order to solve this problem, according to the present invention, there are provided a sample-use light reception unit and main light reception unit and the analogue signal from the sample-use light reception unit and a reference value that is found beforehand are compared and the gain of a variable gain type exponential amplification circuit is set in accordance with the result of this operation; if the amount of light transmitted is expressed by mantissa portion×exponent, where the value of the A/D converter is the mantissa portion, the degree of amplification (gain) of the variable gain type exponential amplification circuit is the base, and the set value thereof is the exponent portion, and the gain can be set continuously to an optimal value within the range of digital resolution of the variable gain type exponential amplification circuit.

In view of the circumstances described above, in online non-destructive inspection of for example fruit or vegetables using for example near infra-red light the problem that is sought be solved by the present invention is to provide a spectrophotometer wherein measurement can be performed that can cope with changes of feeding speed and that provides a high rate of processing and high accuracy and stability without either saturation of the data level or a data level that is too small, in respect of articles to be measured whose amount of transmitted light differs greatly, even for the same type of article, depending on differences in density of fruit or vegetables, differences of skin thickness, or differences of size and the like.

As is common knowledge, the CPUs that are incorporated in present-day computers have high clock speed and large capacity, making possible very fast computational processing. Consequently, equipment performance and cost is largely governed by the method in which they are used i.e. how the digital system and analogue system are allocated and matched.

In contrast to ordinary spectrophotometers used in research laboratories, with spectrophotometers for industrial use, the main patterns of wavelength characteristics, such as for example the maximum and minimum values of amount of transmitted light, magnitude thereof and wavelengths that are highly correlated with sugar content of articles to be measured are known or can be predicted. Consequently, the necessary correction functions of the wavelength characteristics and constants etc can be set at the parameter level and it is possible to predetermine at the design stage for example the range of variation of gain in the amplification circuit.

In this way, a spectrophotometer of high resolution, high dynamic range and low cost can be provided by performing noise reduction by using an analogue system and expressing the degree of resolution of the analogue circuit digitally to the maximum extent, to provide an automatic sensitivity adjustment (auto-gain) function, by employing a rational construction of the spectrophotometer system that is capable of for example effectively adopting floating point decimal operation processing using digital operation with much higher accuracy than the accuracy of a hardware system. This is described below:

In order to solve the problems described above, a spectrophotometer according to the present invention comprises: light emission means that emits light; a main light reception unit having a group of charge accumulation type photodetection elements, which receive, for each wavelength, of the light emitted from the light emission means, incoming light after the light has been transmitted through an article to be measured and been spectrally separated by a spectrometer such as a diffraction grating, and which convert the light into an amount of charge to be accumulated; a sample-use light reception unit for accumulating, in the form of an amount of charge, said incoming light that has been spectrally separated and reading the charge of a specified wavelength or specified wavelength band; a pre-amplifier and drive circuit of said main light reception unit and sample-use light reception unit; a variable-gain type amplification circuit whose gain can be varied by a digital instruction; a zero-point compensation circuit provided in the vicinity of at least the final stage of an analogue circuit unit for sequentially acquiring the zero-point of all the amplification systems immediately prior to sequential reading of the charge accumulated on the pixels of said main light reception unit and sample-use light reception unit; and an A/D converter for converting the analogue voltage from the zero-point compensation circuit to a digital value; and further comprising digital comparison operation means that, in reading the charge accumulated on said main light reception unit and sample-use light reception unit during measurement, first of all amplifies the analogue voltage from said sample-use light reception unit in said variable-gain type amplification circuit set to a low gain at which obviously the maximum point of the wavelength characteristic of a specified wavelength or specified wavelength band is not saturated, and then, after the amplified analogue voltage has passed through said zero-point compensation circuit, subjects the same to A/D conversion in said A/D converter, and performs a digital comparison operation of the digitally converted digital value with a reference value which is finally obtained by being read from said main light reception unit, and which is predetermined as an optimum value such that there is no possibility of the maximum point of the wavelength characteristic at the required wavelength or wavelength band being saturated, and such that the number of significant digits of the digital value is not reduced; means for performing computation when performing this digital comparison operation including a previously prepared pixel unit correction function that corrects the optical absorbance characteristic of the article to be measured such as fruit or vegetables; gain setting means for setting the gain of said variable gain type amplification circuit in accordance with the operation result from the digital comparison operation means; and digital data reading means for acquiring a wavelength characteristic by sequentially reading the group of charges accumulated on said main light reception unit as digital data, in pixel units, through said pre-amplifier and drive circuit, said variable gain type amplification circuit, said zero-point compensation circuit and said A/D converter.

By performing zero-point correction of all of the amplification systems immediately prior to sequential reading of the charge accumulated on the sample-use light reception unit and main light reception unit as described above, noise reduction of the pixel units is achieved; and by raising the sensitivity with an analogue system in the low-level section of the transmitted light amount characteristic of the article to be measured, without employing a logarithmic amplifier, the advantages thereof can be preserved and the drawbacks thereof ameliorated and a spectrophotometer thus obtained having an automatic sensitivity adjustment (auto-gain) function having performance greatly exceeding that of a spectrophotometer using a logarithmic amplifier.

As the sample-use light reception unit, an optical input window may be arranged in an optical region of a specified order of a diffraction grating for light incident of a specified wavelength in the vicinity of the maximum value of the light transmission amount characteristic of the article to be measured, and means may be arranged for guiding light by an optical fiber to the vicinity of a pixel position at the start of reading of a group of charge accumulation type photodetection elements, or a photodiode or photodiode array may be arranged in the position of an optical input window of an optical region in a specified order of a diffraction grating.

In general, the absorption of light by moisture in fruit or vegetables or the like shows a maximum value of the waveform at a specific wavelength where the absorption is least i.e. a wavelength in the vicinity of the maximum value of the transmitted light amount characteristic of the article to be measured; if the gain of the variable gain amplifier is set such that this point approaches a pre-set value, an excellent signal level can be obtained irrespective of the size of the article to be measured without either the signal level becoming too low or the signal level becoming saturated.

The amount of light transmitted may be expressed as: mantissa × exponent, where an exponential type (amplification circuit) is employed for the (digitally set) variable-gain type amplification circuit, the value of the A/D converter representing the mantissa and the set value of the (digitally set) variable gain type exponential amplification circuit representing the exponent portion (the degree of amplification of this circuit being the base and the exponent thereof being the set value).

Typically, for quantization of an analogue signal obtained from the transmitted amount of light of an article to be measured, an amplifier and A/D converter were employed simply to bring this signal to the necessary level and the input level was expressed solely by the mantissa, which is the value of the A/D converter.

In contrast to this, a representation is herein employed in which the transmitted amount of light is represented by mantissa×exponent, by dividing the representation into an mantissa portion (A/D converter portion) and exponent portion (variable-gain type exponent amplification circuit portion).

Specifically, in the conventional type of spectrophotometer, for a transmitted light amount (It), the measured value (A) is expressed by:

$$A = It \times G.$$

In the present invention, the degree of amplification is given by $G_M^X$ and $A = It \times G_M^X$ where the A/D conversion value is (A), the maximum gain of the variable gain type exponential amplification circuit portion is ($G_M$) and the digital resolution is (Nm).

Taking the set value as (N), x=N/Nm and the amount of light transmitted (It) is expressed by $$It = A \times G_M^{-(N/Nm)} \quad \text{Equation 1}$$

where N=0, 1 ... Nm.

According to the present invention, the exponent (N) of the exponent portion is set by comparison of the value of the sample-use light reception unit and a reference value such that the value (A) of the mantissa portion (A/D converter) obtained by the differences in for example amount of transmitted light of the articles to be measured always ensures a sufficient number of significant digits (suitable value) i.e. a number of significant digits that can be measured.

Also at this point, the base ($G_M$) of the exponent portion is the maximum gain of the variable-gain type exponential amplification circuit and the deviation of the mantissa portion is determined by the resolution (Nm) of the exponent portion, the dynamic range being ($A \times G_M$).

For instance, even if a maximum gain ($G_M$=100 times) of the variable-gain type exponential amplification circuit, a digital resolution thereof of (Nm=8) bits, and A/D converter of (A=12) bits are employed, a spectrophotometer of high level having a dynamic range of 4095×100=409500 and a resolution of 12+8=20 bits can be obtained.

From the above, with the system described above, in regard to the resolution and dynamic range of an analogue system, it is possible to achieve a system expressing the resolution of the analogue system to the maximum and extending to the limit the dynamic range and S/N ratio of the photodetection elements by effectively adopting floating point operation processing of much higher accuracy used for example in exponential operation of digital computations.

A characteristic feature is that during the reading of the main light reception unit, when performing comparative operation of the value obtained by the sample-use light reception unit with the reference value, computation is performed including a pixel unit correction function, and gain setting is performed by for example successively supplying arbitrary coefficients to the variable-gain type exponential amplification circuit as all the pixels are read.

If the intensity of the light from the light source is denoted by Io (λ) and the intensity of the light transmitted through the article to be measured is denoted by It (λ), we have:

$$It\ (\lambda) = Io(\lambda) \exp\{-dc\epsilon(\lambda)\} \quad \text{Equation 2}$$

and the optical absorbance is $\log\{It\ (\lambda)/Io(\lambda)\} = -dc\epsilon(\lambda)$ Equation 3 where d=optical path length, c=concentration, ϵ=intensity of absorption of specified wavelength (mol absorption coefficient), and λ=wavelength. Thus when light is transmitted through a medium, its intensity is attenuated in accordance with an exponential function. A method of signal processing and computing for calculating sugar content and acidity or the like using multiple regression and P.L.S. etc from the amount of displacement, by for example n-th order differentiation of this optical absorbance characteristic will now be described.

If now the optical absorbance obtained from the spectrophotometer is the pixel level corresponding to the wavelength λ, specifying the pixel as p, this can be expressed as:

$$\log A/B = -dc\epsilon(p) \quad \text{Equation 4}$$

where $A = Q[Ga \cdot Gk(p)[It\ (p) - Id(p)]]$, and $B = Q[Gb \cdot Gk(p)[Ir(p) - Id(p)]]$, for $p = 0, 1 \ldots n$ A, B=Q [x] indicate quantization functions i.e. that x is converted to digital form.

It (p): this is the absorption waveform obtained at the target when the light from the light source is transmitted through the article to be measured; depending on the construction of the feed mechanism, it may include a considerable amount of light that reaches the target without passing through the article to be measured.

Ir (p): this is a reference, corresponding to $I_0$ (p) and may be some $10^5$ times It (p); using an ND filter or the like of flat wavelength characteristic, attenuation takes place to the It level; it expresses in the form of a reference the change with time of the light source and the specific wavelength characteristic of the entire spectrophotometer system.

Id (p): this is an offset, providing the basis for It (p) and Ir (p), taking as an offset value the values of all the signal amplification systems including the dark current of the sensor in the zero light condition.

Ga: this is an auto-gain coefficient; Ga is obtained by a digital comparison operation of the A/D conversion value obtained by the amount of transmitted light of the article to be measured typically read under low gain obtained from the sample-use light reception unit and a reference level determined in order for a required point, for example the maximum point thereof, of the wavelength characteristic of the article to be measured, when read at the main light reception unit, to approach the maximum value of the A/D converter.

Gb: this is the gain coefficient and is a coefficient set in the variable-gain type exponential amplification circuit in order for an optimum reference or offset value to be obtained.

Gk (p): this is a pixel unit correction function: for example, in order to increase the gain in the low level region in a manner corresponding with the wavelength characteristic of the articles to be measured, specifically, in order to amplify the low region, taking the vicinity of the maximum point of the amount of transmitted light of the wavelength characteristic of the article to be measured as 1, for example a function is prepared based on a coefficient comprising a predetermined data group and the results of pixel reading of the sensor multiplied by Ga are successively set in the variable-gain type exponential amplification circuit.

Specifically, in the measurement of articles to be measured whose amounts of transmitted light differ greatly, first of all the level of a specified wavelength in the vicinity of for example 820 nm is measured by the sample-use light reception unit and the gain of the variable-gain type amplification circuit is set by performing a comparative operation with a reference level that is set such as to ensure that the digital value obtained by the A/D converter has a sufficient number of significant digits deemed necessary for calculation; and, when reading the charge of the main light reception unit, noise reduction is performed in the analogue circuit by performing zero-point correction of all of the amplification systems successively prior to reading: thus, A/D conversion can be performed on a suitable analogue level.

There is therefore no possibility of the spectral data being saturated or too low and it is possible to cope with changes in feed speed (and the exposure time corresponding thereto). A spectrophotometer can be provided having extremely large dynamic range with high speed and low noise and having an automatic sensitivity adjustment (auto-gain) function, without employing a high resolution A/D converter, which is expensive and has a low processing speed, or an expensive logarithmic amplifier.

By expressing the amount of transmitted light (spectral data) by: mantissa×exponent, using an exponential type amplification circuit for the variable-gain type amplification circuit, taking the value of the A/D converter as the mantissa portion and taking the value of the variable-gain type exponential amplifier circuit as the exponential portion (the maximum gain of this circuit being the base and the exponent being the set value), troublesome calculation to find the optimum gain becomes unnecessary and the deviation of the mantissa portion produced by differences in amount of transmitted light is determined by the resolution of the exponential portion. In this way, for the data group obtained by the A/D conversion, data can always be obtained having a stable and sufficient number of significant figures or number of significant digits, making it possible to obtain data of high accuracy.

When performing comparative operation of the value obtained by the sample-use light reception unit and the reference value during reading of the main light reception unit, computation including a pixel unit correction function is performed, and the operation results are set in the variable-gain type exponential amplification circuit for all the pixels. In this way, optimum gain setting is performed for each pixel unit and data of high accuracy can be obtained over the entire wavelength band.

BRIEF DESCRIPTION OF THE DRAWINGS

FIG. 5 (a) is a plan view showing a line sensor and sample-use light reception unit, and (b) is a plan view showing a line sensor and another sample-use light reception unit.

DESCRIPTION OF THE PREFERRED EMBODIMENTS

Figure 1:
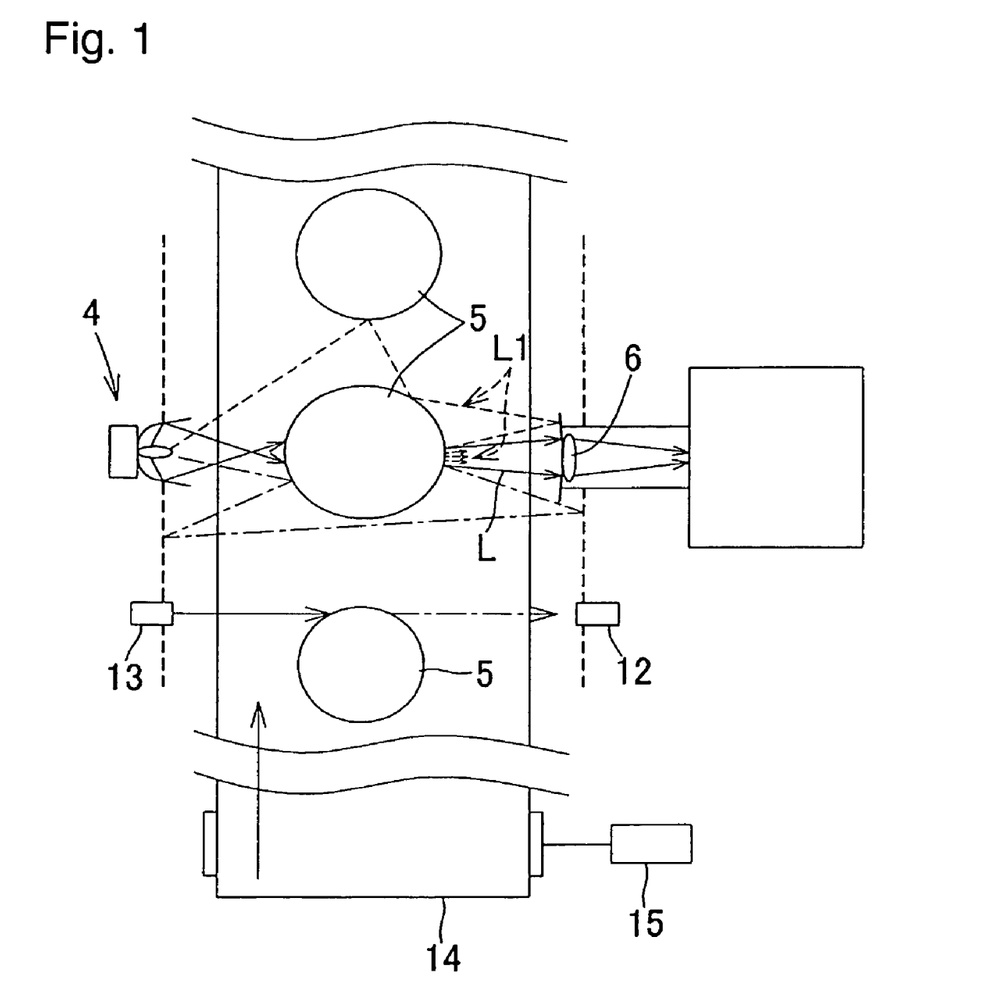
FIG. 1 Plan view showing the arrangement of a spectrophotometer that measures the internal properties of fruit or vegetables.
Figure 2:
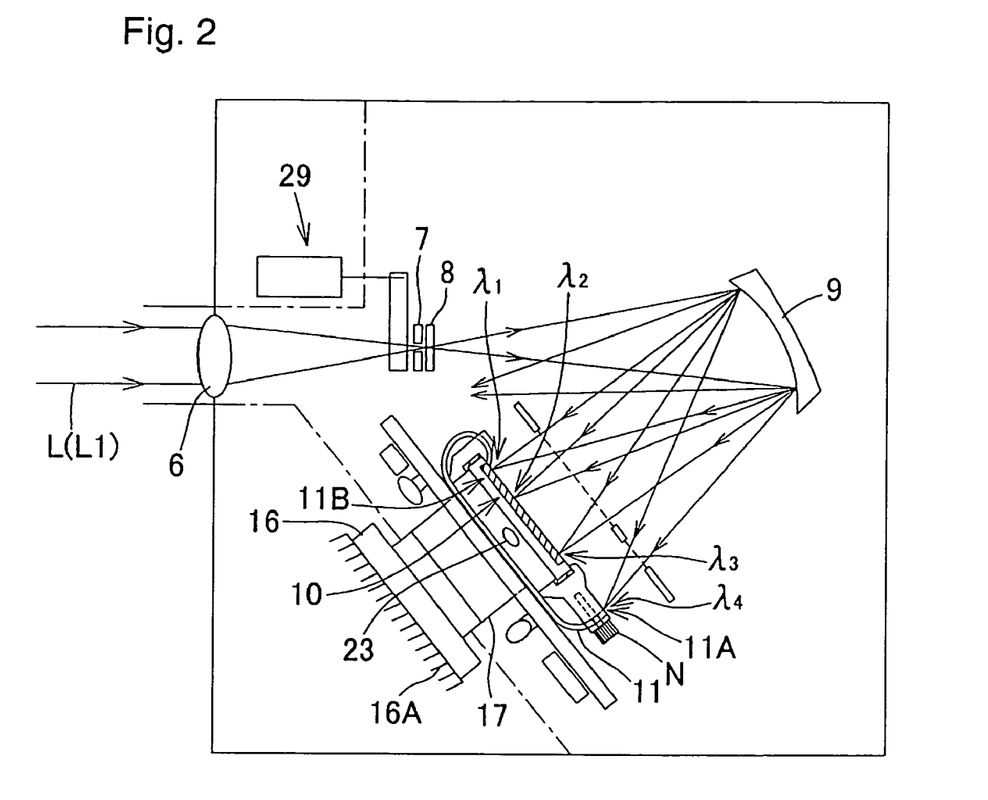
FIG. 2 Partially sectioned diagram showing the specific construction of the interior of the spectrophotometer.

FIG. 1 and FIG. 2 show a specific construction of a spectrophotometer for measuring for example sugar content or acidity of the fruit or vegetables 5 constituting articles to be measured. This spectrophotometer comprises: a condensing lens 6 that receives for example transmitted light L that has been transmitted through the fruit or vegetables 5 from light emission means 4 such as a halogen lamp and light L1 therefrom that has not passed through the fruit or vegetables 5; a diffraction grating 9 that performs spectral separation of light that has passed through this condensing lens 6 after it has passed through a slit 7 and high cut-off filter 8; a line sensor 10 constituting a main light reception unit comprising a group of charge accumulation type photodetection elements for detecting light of each wavelength of first-order light $\lambda 1$ (600 nm) to $\lambda 3$ (1100 nm) obtained by spectral separation performed by this diffraction grating 9 and converting this into an amount of charge, which is accumulated; and an optical fiber 11 with a photodetection window 11A arranged at one end, so that the amount of light in the vicinity of $\lambda 4$ (820 nm), which is the second-order light of $\lambda 2$ (820 nm) can be read as an amount of charge; the other end of this optical fiber 11 is led to the vicinity of the initial read pixel (0) of the line sensor 10, thereby constituting a sample-use light reception unit 11B, from which sample light is obtained. 12 shown in FIG. 1 is a photodetection unit of the photoelectric type for detecting light from a photoelectric light emission unit 13 and is arranged so as to be capable of ascertaining that fruit or vegetables 5 has moved to a prescribed position by interruption of light from the light emission unit 13 by fruit or vegetables 5 fed by a belt conveyor 14. Also, 15 shown in FIG. 1 is a rotary encoder for detecting for example the speed of rotation of the belt conveyor 14; the detection signal from the rotary encoder 15 and photoelectric light detection and emission units 12, 13 is applied to CPU 1 and 2, to be described, in order to obtain for example the feed speed of the belt conveyor 14, the size of the fruit or vegetables 5, the read timing of the fruit or vegetables 5, and the exposure time of the line sensor 10, based on the detection pulse number of this rotary encoder 15 and the time of interruption of light by the fruit or vegetables 5 at the photoelectric light detection and emission units 12, 13 (these two items will hereinbelow be referred to as a conveyor speed/fruit or vegetable size measuring unit, to be described). 29 shown in FIG. 2 is a switch actuator for reference and offset. As described above, apart from the transmitted light L that has been transmitted through the fruit or vegetables 5, light L1 that has propagated around these or light that has been reflected by the fruit or vegetables, or diffused light etc is collected by the condenser lens 6. N shown in FIG. 2 is an adjustment screw for adjusting the photodetection position of the sample photodetection window 11B.

The necessary level (reference value) for aligning the maximum values is calculated from the values of the initially read pixel data of the line sensor 10 and gain correction is applied in pixel units to the pixels (4, 5 . . . , n) of the main light reception unit in respect of the pixels (0, 1, 2, 3) and subsequent pixels of the sample-use light reception unit and these gains are successively set in the variable-gain type exponential amplification circuit, for each pixel.

Figure 5:
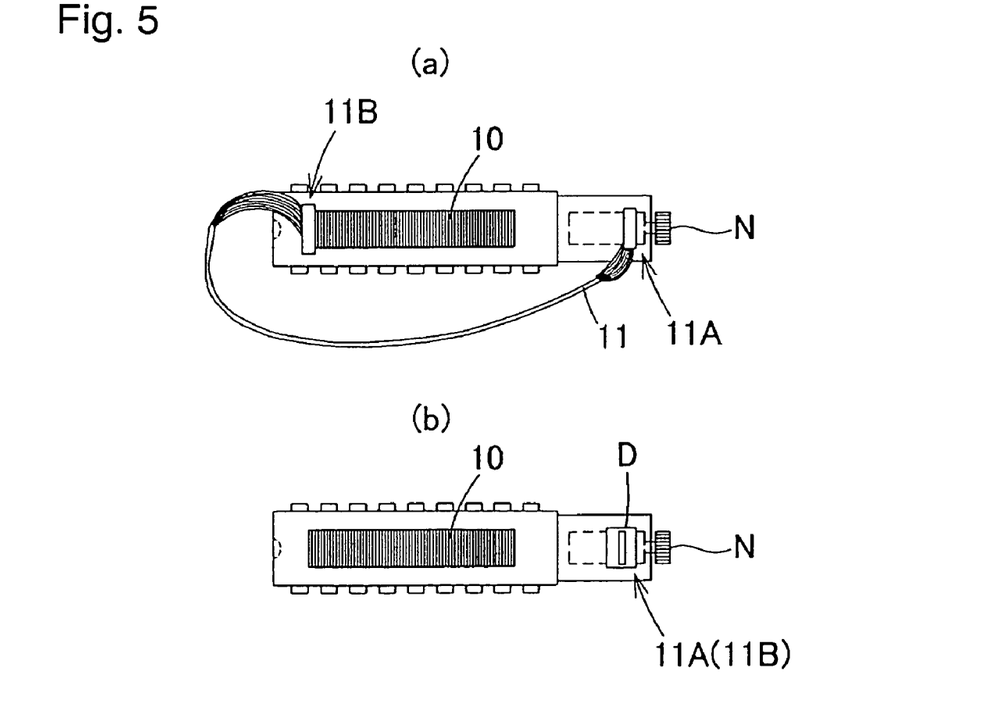

FIG. 5(a) is a plan view of a photodetection unit wherein an optical fiber 11 is employed in the sample-use light reception unit of FIG. 2 and whereby sample light is directed to the charge accumulation type line sensor 10 itself.

By employing a plurality of pixels (0, 1, 2 . . . ) of the line sensor 10 referred to above, a margin in respect of optical accuracy can be obtained and the S/N ratio of the signal can be improved by averaging the signals of this plurality of pixels.

Compared with the use of another photodiode D as in FIG. 5(b), the advantage is obtained that the construction is much simpler, in that there is no need to consider for example addition of a charge-voltage conversion circuit and the corrections that are thereby entailed.

Also, FIG. 5(b) is a plan view of a photodetection unit in which is arranged a photodiode D such as to input light in the vicinity of the aforesaid λ4 (820 nm), as with an optical fiber. If such a component arrangement construction is adopted, although for example a charge-voltage conversion and amplification circuit of the photodiode D constituting the sample photodetection window is necessary, the step of mounting an optical fiber on a line sensor can be dispensed with. Furthermore, the position of photodetection in the photodiode D of λ4 (second-order light) is adjacent to the position of installation of the line sensor 10 and, as shown in FIG. 2, these can thus both be incorporated with a temperature-controlled block that is adjusted in temperature through a heat conduction plate 17 from a Peltier element 16. 16A shown in FIG. 2 are radiating fins for radiating heat from the Peltier element 16.

By using the aforesaid λ4 (second-order light), an extremely rational construction is achieved in which inevitable use of a band pass filter of 820 nm is unnecessary; however, if required, zeroth order light could be employed.

Of course, systems may also be considered in which a plurality of optical fiber circuits are employed or an arbitrary wavelength is selected by using a photodiode array for the photodiode D, or systems in which both these are combined, having a construction in which an optical input unit of optical fiber 11 from outside and photodiode D are moved to arbitrary positions.

Also, achieving the object with for example light of the same order by using an area sensor as the sensor may be considered.

Next, a block diagram of the spectrophotometer shown in FIG. 3 will be described.

The arrangement of the pixels (photodiodes) of the line sensor 10 corresponds to the spectrum produced by the spectral separation achieved by the diffraction grating 9, these being arranged in sequence from short wavelength to long wavelength from the pixel (0) to the pixel (511). Also, a charge accumulation type photodetection element group 18 and preamplifier and sensor drive circuit 19 are provided in order to accumulate charges corresponding to the respective spectral components. The charge accumulation time and reading timing are controlled by the CPUs 1 and 2 and an analogue signal is output proportional to the accumulated charge in synchronization with the clock pulse from the CPUs 1 and 2. If a photodiode type unit is employed for the sample-use light reception unit 11, a switch circuit is required for changing over a circuit such as the aforesaid circuit 19 and line sensor. In this block diagram, as described above, as the sample-use light reception unit, one end of the optical fiber 11 is mounted in the vicinity of the pixels (0, 1, 2, 3) while the other end thereof is mounted in the position of the wavelength where the amount of transmitted light by the article to be measured on the second order light from the diffraction grating 9 is greatest.

Figure 3:
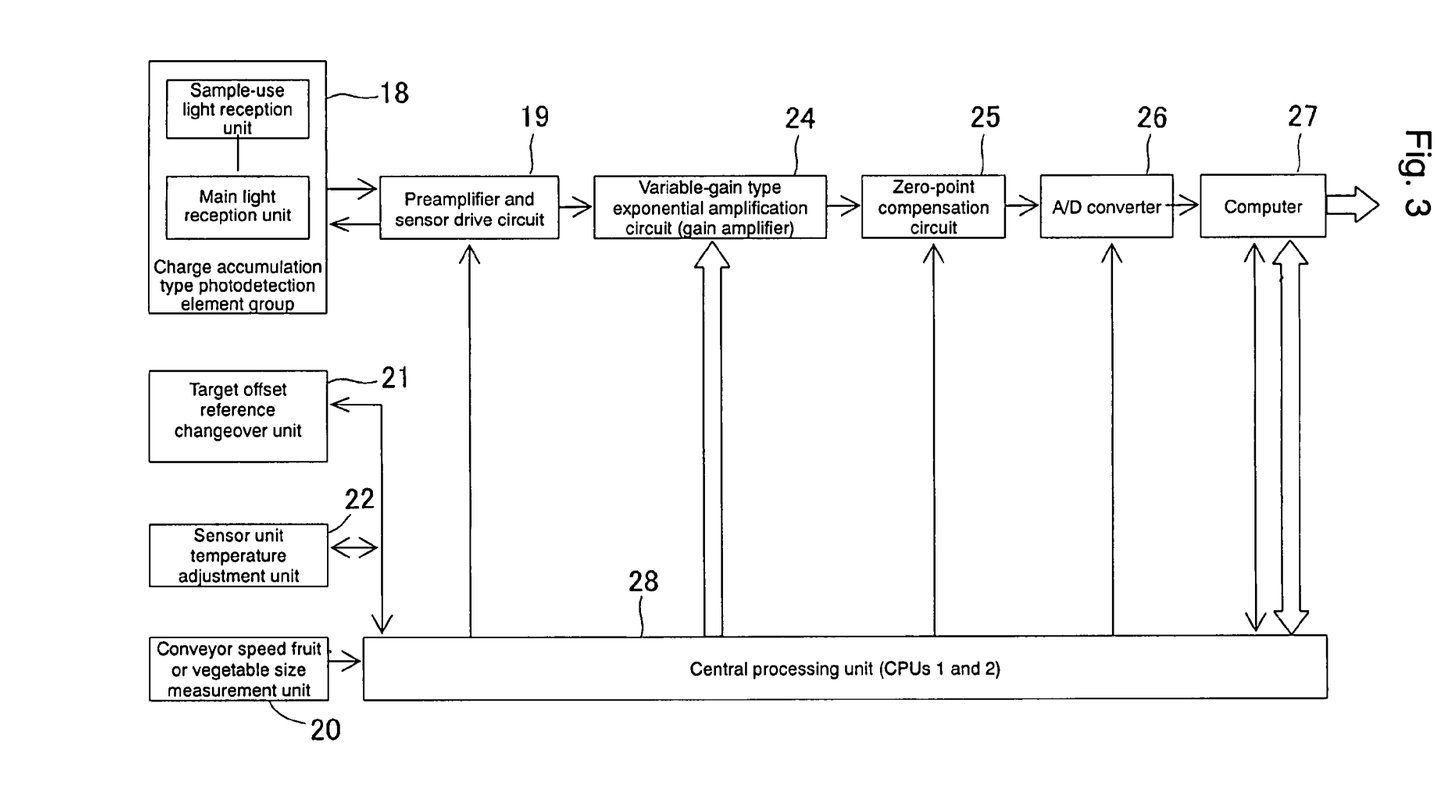
FIG. 3 Control block diagram.

The size (dimensions) of the fruit or vegetables and the speed of the belt conveyor 14 are calculated by the CPUs 1 and 2 using the signal obtained by the conveyor speed/fruit or vegetable size measurement unit 20 shown in FIG. 3. In this way, an effective charge accumulation time is set and the line sensor 10 commences charge accumulation from the time-point where the optimum reading position of the fruit or vegetables reaches the optic axis.

21 shown in FIG. 3 is a changeover unit for changing over optically the three factors: target, offset and reference, under the control of an actuator 29; a position detection section and drive section thereof are linked with the CPUs 1 and 2, so that, if required, a single one of these three factors can be selected. In actual operation, the size and the gaps of the fruit or vegetables move irregularly over the belt conveyor 14. Calculation of the optical reference (ND filter) and offset (optical screening) of the spectrophotometer is performed in accordance with the speed of movement and the condition regarding the intervals of the fruit or vegetables, during these gaps.

22 shown in FIG. 3 is a sensor unit temperature adjustment unit for monitoring the temperature of the Peltier element by means of the temperature sensor 23 shown in FIG. 2 and controlling the temperature of the sensor unit to a suitable temperature by performing PID temperature control using the CPUs 1 and 2.

18 shown in FIG. 3 is a group of charge accumulation type photodetection elements: for the main light reception unit, a charge accumulation type line sensor (current output type) is employed; for the sample-use light reception unit, a charge accumulation type sensor is employed in which reverse bias voltage is applied to a photodiode.

19 shown in FIG. 3 is a preamplifier and sensor drive circuit: this drives the sensor unit under the control of signals from the CPUs 1 and 2, this drive timing being synchronized with that of the zero-point compensation circuit. In this case, the sensor drive circuit is of a type incorporating a charge-voltage conversion circuit.

24 shown in FIG. 3 is a digitally controlled exponential amplification circuit (also referred to as a variable-gain type exponential amplification circuit or simply gain amplifier) for obtaining a prescribed gain by converting the data from the CPUs 1 and 2 to analogue voltage by means of a D/A converter, not shown, and applying this analogue voltage to the gain control input terminal of a voltage controlled exponential amplifier; the gain of this digitally controlled exponential amplification circuit 24 is thus set by a digital instruction from the CPUs 1 and 2 in accordance with the digital signal from an A/D converter 26, to be described. The value of $G_M$ (the maximum gain), which is the base of the gain, is also set.

25 shown in FIG. 3 is a zero-point (0 line) compensation circuit for setting a base line with the significance of a zero for the electrical signal system and for fixing the value immediately prior to arrival of the analogue signal synchronized with the signal synchronization pulse amplified by the aforesaid circuits 19 and 24 to the value at this baseline: it comprises a clamp and filter circuit.

26 in FIG. 3 is an A/D converter for converting the analogue signal regenerated by the zero-point compensation circuit 25 to digital form and has a sample-hold function at the input unit.

27 in FIG. 3 is a computer in which the data of the A/D converter 26, the set value (exponent value) of the gain amplifier 24, the size of the fruit or vegetables and the exposure time are written in the shared memory of the CPUs 1 and 2 with the control timing from the CPUs 1 and 2; this computer performs necessary signal processing operations from this stored data and determines the contents of sugar, acid and other items by for example multiple regression analysis and P.L.S. analysis and outputs the results.

29 shown in FIG. 3 is a central processing unit comprising a CPU 1 and CPU 2 for performing the main control operations of the online spectrophotometer. This comprises: digital comparison operation means that performs digital comparison operation of a predetermined reference value (value finally obtained by reading from said main light reception unit and determined such that it is an optimum value at which the maximum point of the wavelength characteristic of a wavelength or wavelength band required for analysis of the articles to be measured is not saturated and further such that the number of significant digits of the digital value is not reduced) and a digital value obtained by reading, through said zero-point compensation circuit 25, the amplified analogue voltage, which is an analogue voltage from the sample-use light reception unit, amplified by said variable-gain type amplification circuit 24, which is set to a pre-set fixed gain (i.e. a low gain at which it is clear that the maximum point of the wavelength characteristic of a specified wavelength or specified wavelength band required for analysis of the articles to be measured is not saturated), and converting this to digital form by A/D conversion, using said A/D converter 26, of the analogue voltage thus obtained; gain setting means that sets the gain of said variable-gain type amplification circuit 24 such that the operation result i.e. the digital value from the A/D converter 26 from said digital comparison operation means substantially coincides with the reference value, in other words such that the digital value from the A/D converter 26 becomes an analogue level necessary for securing the number of significant digits that can be measured; and digital data reading means that reads the group of charges accumulated on said main light reception unit sequentially in pixel units as digital data through said preamplifier and sensor drive circuit 19, said variable-gain type amplification circuit 24, said zero-point compensation circuit 25 and said A/D converter 26.

INDUSTRIAL APPLICABILITY

A spectrophotometer according to the present invention is advantageous in particular for measuring for example sugar content or acidity of fruit or vegetables as they are fed, but it can also be applied for example to measurement of the internal properties of potatoes or onions and the like.

The invention claimed is:

1. A spectrophotometer to analyze an article to be measured, the spectrophotometer comprising:
(a) light emission means that emits light onto the article to be measured;
(b) a light-dispersing spectrometer receiving light from the article;
(c) a main light reception unit including a group of charge accumulation type photodetection-element pixels which receive, for various wavelengths or wavelength bands of light emitted from the light emission means, light that has been transmitted through the article to be measured and has been spectrally separated by the spectrometer and wherein the photodetection-element pixels convert the light into an amount of charge to be accumulated;
(d) a sample-use light reception unit for accumulating, in the form of an amount of charge, a portion of said incoming light simultaneously with said main light reception unit and reading the charge of a specified wavelength or specified wavelength band of said incoming light;
(e) an analogue circuit unit further comprising:

a pre-amplifier and drive circuit coupled to said main light reception unit and sample-use light reception unit;
a variable-gain type amplification circuit whose gain can be varied by a digital instruction; and
a zero-point compensation circuit, provided in the vicinity of at least a final stage of said analogue circuit unit, to sequentially acquire the zero-point of all the amplification circuits immediately prior to sequential reading of the charge accumulated on the pixels of said main light reception unit and sample-use light reception unit;
(f) an A/D converter, coupled to the analogue circuit unit, for converting the analogue voltage from the zero-point compensation circuit to a digital value;
(g) digital comparison operation means that, in reading the charge accumulated on said main light reception unit and sample-use light reception unit during measurement,
first of all amplifies the analogue voltage from said sample-use reception unit in said variable-gain type amplification circuit that is set to a low gain at which an expected maximum point of the wavelength characteristic of a specified wavelength or specified wavelength band is not saturated, and
then, after the amplified analogue voltage has passed through said zero-point compensation circuit, subjects the analogue voltage to A/D conversion in said A/D converter, and
performs a digital comparison operation of the digitally converted digital value with a predetermined reference value, which is finally obtained by being read from said main light reception unit, and which is predetermined as an optimum value such that there is no possibility of the maximum point of the wavelength characteristic at a required wavelength or wavelength band being saturated, and such that the number of significant digits of the digital value is not reduced;
(h) gain setting means for setting the gain of said variable gain type amplification circuit in accordance with an operation result from the digital comparison operation means; and
(i) digital data reading means for acquiring a wavelength characteristic by sequentially reading the group of charges accumulated on said main light reception unit as digital data, in the pixels, through said pre-amplifier and drive circuit, said variable gain type amplification circuit, said zero-point compensation circuit and said A/D converter after setting the gain in said variable-gain type amplification circuit by the gain setting means.

2. The spectrophotometer according to claim 1, wherein said spectrometer comprises a diffraction grating, and wherein said sample-use light reception unit includes an optical input window that is arranged in an optical region in a specified order of a diffraction grating for light incident of a specified wavelength in the vicinity of the maximum value of the light transmission amount characteristic of the article to be measured; and comprising means for guiding light by an optical fiber to the vicinity of a pixel position at the start of reading of a group of said charge accumulation type photodetection element pixels, or a photodiode or photodiode array that is arranged in the position of an optical input window in an optical region of a specified order of said diffraction grating.

3. The spectrophotometer according to claim 1, wherein the amount of light transmitted is expressed as: mantissa×exponent, where the digital value of said A/D converter represents the mantissa, said variable-gain type amplification circuit is an exponential type amplification circuit, the maximum set gain thereof being the base, the exponent thereof being the set value, and said gain of said variable gain type exponential amplification circuit representing the exponent.

4. The spectrophotometer according to claim 1, wherein, during the reading of said main light reception unit, when performing comparison operation of the value obtained by said sample-use light reception unit with the reference value, computation is performed including a pixel unit correction function, and gain correction in the pixel units is performed by successively setting said operation results in the said variable-gain type amplification circuit as all the pixels are read.

5. The spectrometer according to claim 1, wherein the article to be measured is disposed between the light emission means and the spectrometer.

6. The spectrometer according to claim 5, wherein the spectrometer comprises a diffraction grating.

7. The spectrophotometer according to claim 1, wherein the light from the light emission means is not chopped.

8. The spectrophotometer according to claim 1, wherein each of the photodetection-element pixels corresponds to a respective specified wavelength or specified wavelength band of said incoming light.

9. The spectrophotometer according to claim 1, comprising a first pre-amplifier and drive circuit coupled to said main light reception unit and a second pre-amplifier and drive circuit coupled to said sample-use light reception unit.

* * * * *